United States Patent [19]
Forgac

[11] Patent Number: 5,929,255
[45] Date of Patent: Jul. 27, 1999

[54] PROCESS FOR COPRODUCING FUMARIC ACID AND MALEIC ANHYDRIDE

[75] Inventor: John M. Forgac, Elmhurst, Ill.

[73] Assignee: BP Amoco Corporation, Chicago, Ill.

[21] Appl. No.: 08/890,059

[22] Filed: Jul. 9, 1997

Related U.S. Application Data

[60] Provisional application No. 60/021,541, Jul. 11, 1996.

[51] Int. Cl.[6] .......................... C07D 307/60; C07C 51/00; C07C 51/087
[52] U.S. Cl. ........................... 549/258; 549/257; 549/262; 562/591; 562/595
[58] Field of Search ..................................... 549/262, 257, 549/258; 562/591, 595

[56] References Cited

U.S. PATENT DOCUMENTS

| | | | |
|---|---|---|---|
| 2,500,260 | 3/1950 | Newton ..................................... | 562/591 |
| 3,657,333 | 4/1972 | Ackermann et al. ................ | 260/527 R |
| 3,865,849 | 2/1975 | Garkisch et al. ................ | 260/346.8 M |
| 3,873,577 | 3/1975 | Garkisch et al. ................ | 260/346.8 M |
| 3,993,671 | 11/1976 | Ramioulle ............................. | 260/346.8 |
| 4,191,695 | 3/1980 | Neri et al. ........................... | 260/346.76 |

FOREIGN PATENT DOCUMENTS 2098612  11/1982  United Kingdom .

OTHER PUBLICATIONS

Dr. Kurt Lohbeck, Veba Chemie AG/Werk Bottrop Postfach 740, 425 Bottrop "Experience With Continuous Maleic Acid Anhydride Distillation by the Veba–Chemie/Lurgi Method". Presented at the Fourth Communal Conference OGEW/DGMK on Oct. 4–6, 1976 in Salzburg.

*Primary Examiner*—Bernard Dentz
*Attorney, Agent, or Firm*—Mary Jo Kanady; Wallace L. Oliver

[57] ABSTRACT

The present invention provides a process for recovering fumaric acid formed as a by-product during the production of maleic anhydride so that both fumaric acid and maleic anhydride are obtained. The process of the present invention further eliminates the wasting of MAN that occurs when fumaric acid is incinerated and improves the production of maleic anhydride by eliminating a source of fouling caused by the fumaric acid which leads to down-time in the reaction process to clean out the fumaric acid.

52 Claims, 4 Drawing Sheets

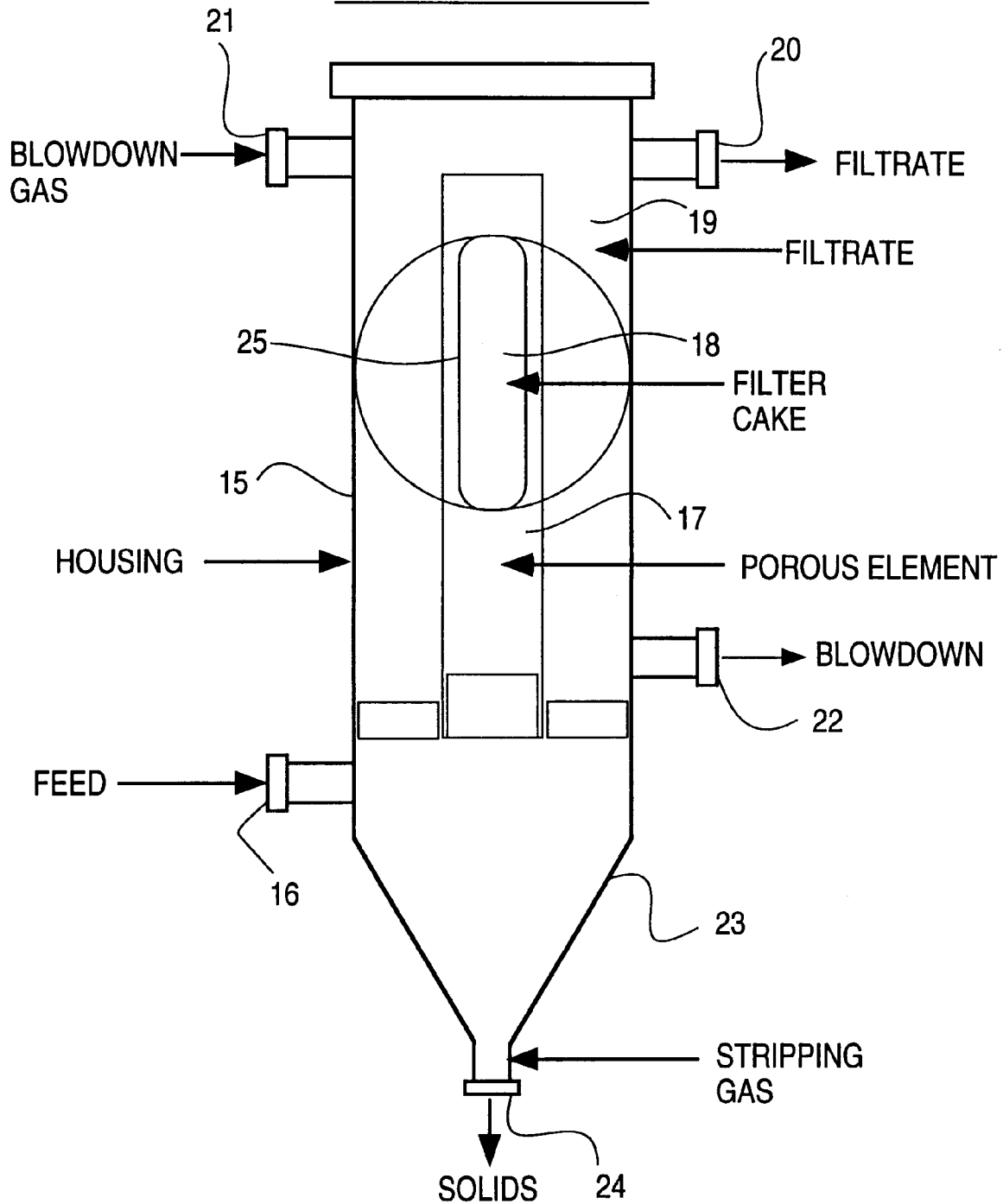

PROCESS FOR COPRODUCING FUMARIC ACID AND MALEIC ANHYDRIDE

This application claims the benefit of U.S. Provisional Application No. 60/021,541 filed Jul. 11, 1996, which is incorporated herein by reference in its entirety.

FIELD OF THE INVENTION

The present invention relates to a process for coproducing fumaric acid and maleic anhydride from an aqueous maleic acid (MA) solution obtained from the gas phase oxidation of butane or another hydrocarbon having four carbon atoms. Fumaric acid (FA) is produced as a by-product during the production of maleic anhydride (MAN); however, without the means to recover the fumaric acid, this material is wasted, providing no economic benefit. The present invention provides a process for recovering fumaric acid formed as a by-product during the production of maleic anhydride so that both fumaric acid and maleic anhydride are obtained. The process of the present invention further eliminates the wasting of MAN that occurs when fumaric acid is incinerated and improves the production of maleic anhydride by eliminating a source of fouling caused by the fumaric acid which causes down-time in the reaction process.

BACKGROUND OF THE INVENTION

Maleic anhydride is of significant commercial interest throughout the world and is extensively used in the manufacture of alkyd resins and as an intermediate for chemical synthesis among other things. Fumaric acid is also of significant commercial interest and is used in the manufacture of inks, in paper sizing, in unsaturated polyesters, and as a food additive among other things.

Maleic anhydride is produced industrially by gas phase oxidation of four-carbon hydrocarbons such as benzene, butane, butenes, and butadiene, etc., in the presence of suitable catalysts and oxygen. The maleic anhydride thus formed may be separated subsequently in the solid or liquid state in suitable separators. Part of the maleic anhydride formed passes in gas form through a separator and must be washed out of the gas stream with water or suitable absorption agents. When water is used as a washing agent, concentrated aqueous maleic acid solutions result. This maleic acid must then be converted to maleic anhydride.

A common method used to convert the maleic acid to maleic anhydride is to remove the water by azeotropic distillation under atmospheric pressure in the presence of a suitable organic solvent entrainer, such as o-xylene or another xylene, pseudocumene, etc. which removes the solution water and splits off one mole of water to convert the maleic acid to maleic anhydride. The organic solvent may then be removed by distillation and the crude maleic anhydride further purified if desired.

Another method of converting the maleic acid to maleic anhydride is to remove the water by vacuum distillation during which the maleic acid is converted to maleic anhydride at temperatures of 150° C. to 160° C. (302° F. to 320° F.). In this method the maleic acid to maleic anhydride conversion takes place by thermal treatment in the presence of a solvent which may be o-xylene or another suitable organic solvent or maleic acid anhydride.

A major disadvantage of the thermal vacuum distillation is that the high temperatures needed for the thermal treatment cause a significant portion of the maleic acid to isomerize to fumaric acid. The fumaric acid, which is insoluble or only slightly soluble under reaction conditions, has a high melting point and causes clogging of valves, pipes and pumps, as well as deposits in the vessels, which represents a loss in yield and requires that the manufacturing installation be shut down periodically in order to clean the units and remove the fumaric acid that has collected and is fouling the connecting apparatus. Such shut downs are costly and reduce the efficiency of the maleic anhydride production process.

OIL GAS J., v.72, n. 36, 103 Sep. 9, 1974 discloses a continuous recovery of pure maleic anhydride wherein fumaric acid is removed down to a residual content of 0.1 wt. % by filtration in the first stage prior to dehydration. In the second stage the residual maleic acid in the crude mixture is converted to maleic anhydride and water, and the water and low boilers are removed. In a third stage the entrainer is removed by distillation, if necessary.

GB 2 098 612 discloses a process for production of fumaric acid from wash waters of exhaust gasses resulting from hydrocarbon oxidation which contain maleic acid. The process comprises a thermal pretreatment of the impure maleic acid solution, with optional concurrent concentration, with transformation of part of the impurities to facilitate their elimination from the final product, subsequent hot filtration, isomerization of the MA to FA using thiourea as catalyst for the isomerization, crystallization according to a pre-set time/temperature chart, removal of the mother liquors by filtration, subsequent dissolution in water or in a fumaric acid solution, decolorization, recrystallization, and drying.

U.S. Pat. No. 3,993,671 (Ramioulle) discloses a continuous process for the preparation of maleic anhydride from an aqueous solution of maleic acid formed in the production of maleic anhydride by the catalytic oxidation of aliphatic or aromatic hydrocarbons, with the continuous elimination of the impurities which accompany this maleic acid solution or which are subsequently formed in the conversion of maleic acid into maleic anhydride comprising the stages:

a. continuously heating the starting aqueous solution of maleic acid in a concentration zone kept at a temperature of 100° to 150° C. and at a pressure of 400 to 760 mm. Hg. in order to obtain molten maleic acid containing 0 to 10% by weight of water and water vapor, and washing said water vapor in order to recover entrained maleic acid therefrom, the aqueous solution of maleic acid thus formed being fed to state (c);

b. continuously feeding the molten maleic acid obtained in stage (a) to a conversion zone kept at a temperature of 115° to 165° C. and at a pressure of 40 to 200 mm. Hg. and consisting of
 I. a liquid suspension composed of a reaction mixture containing about 1 to 20% by weight of maleic acid, 0 to 30% by weight fumaric acid, 99 to 55% by weight of maleic anhydride, and 0 to 5% by weight of resinous residues, and;
 ii. a purified gaseous phase containing maleic anhydride and water vapor, the amount of molten maleic acid added in an hour to the said reaction mixture representing from 10 to 50% of the weight of said reaction mixture;

c. continuously or semi-continuously withdrawing from 0.5 to 5% by weight of the said reaction mixture present in said conversion zone of step (c) per hour, and feeding it to a dissolution and filtration zone, in which it is suspended in the aqueous solution of maleic acid coming from stages (a) and (d), filtering the suspension thus obtained in order to separate a solid cake of fumaric acid and resinous residues, which is discharged from the system, and recycling a liquid filtrate consisting of an aqueous solution of maleic acid, to the starting aqueous solution of maleic acid;

d. continuously condensing the gaseous phase produced in stage (b) at a temperature above the dew point of the water vapor present, the condensate thus obtained being maleic anhydride with a purity of at least 99%, which is recovered as the product of the process, while washing with water the residual water vapor, which still contains entrained maleic anhydride, in order to form an aqueous solution of maleic acid, which is recycled to state (c).

This process differs from the process of the present invention. It uses a two-step dehydration process with a thin film evaporator followed by a still-dehydrator which is operated under vacuum. The MAN product along with water leaves the dehydrator in a gaseous stream overhead. A bottoms purge from this step, containing maleic acid and fumaric acid goes to the filter. The stream being filtered is different; it filters a maleic acid solution which is then recycled to the process. In Ramioulle's process, a purge of the reaction mixture in the still-dehydrator is combined with aqueous maleic acid solutions from other points in the process. This aqueous mixture of maleic acid, fumaric acid and other residue is then passed through the filter. The filtrate is maleic acid and water which is returned to the process upstream.

U.S. Pat. No. 3,657,333 discloses a process for the production of fumaric acid from the residue formed in equipment for refining maleic acid or maleic anhydride especially from the wash waters used in the cleaning of equipment for refining maleic acid or maleic anhydride. The process comprises filtering a hot aqueous solution of the raw fumaric acid (e.g. wash water from the aforementioned equipment) optionally after isomerization of its maleic acid content to fumaric acid, separating from the filtrate the prepurified fumaric acid which crystallizes out upon cooling, and drying the fumaric acid from the filtrate and subjecting it to a thermal treatment at 170°/C. to 240° C. in an oxygen poor atmosphere, dissolving the resulting product in hot water, filtering the hot solution and treating the filtrate with decolorizing agents.

U.S. Pat. No. 4,191,695 discloses a process for obtaining maleic anhydride in which the formation of fumaric acid by-product is avoided by reacting the maleic acid precursor with an organic carboxylic acid anhydride so that an $H_2O$ exchange is carried out between the maleic acid and the organic carboxylic acid anhydride giving as end products maleic anhydride and organic acid. The reaction is said to be conducted at such low temperatures that the customary impurities formed at higher temperatures no longer result and the isomerization of maleic acid into fumaric acid does not occur.

The process of the present invention avoids the problems of equipment fouling caused by FA and provides a process for coproducing FA along with MAN. In the process of the present invention, FA is recovered as a co-product with MAN, when MAN recovery is an aqueous recovery. FA is recovered by employing a separation operation to remove the FA from a stream of molten MAN. The FA is recovered as a solid. If desired, residual MAN may then be removed from the FA solids, by stripping, washing, or other means, to provide a high purity FA. In the preferred process, a sintered metal filter is used. This type of filter withstands the high temperature and corrosive environment when the correct metallurgy is used. The process involves allowing FA to form in a holding tank, pumping the stream containing FA through the filter to recover the FA, recycling the FA-free stream in part to the holding tank with the rest going to further processing. In the preferred form of the process, at least two filters are used in order to provide continuous process performance. When the first filter is full of FA, the flow is switched to the other filter; the FA solids which have been collected on the first filter are stripped with inert gas to remove residual MAN, cooled in a conveying device, and packaged in a shipping bag. When the second filter is full of FA, the flow is switched back to the first filter and the FA solids on the second filter are stripped with gas, cooled in a conveying device, and are ready for packaging. Optionally the FA may be purified further by washing with water following stripping off of the residual MAN with gas.

SUMMARY OF THE INVENTION

The present invention relates to a process for coproducing fumaric acid and maleic anhydride which comprises:

(a) deriving a composition comprising maleic anhydride and fumaric acid, from a system for the catalytic oxidation of butane or another hydrocarbon after dehydration;

(b) cooling said composition sufficiently to precipitate the fumaric acid;

(c) separating the fumaric acid precipitate from step (b) from the maleic anhydride, and recovering the fumaric acid; and (d) recovering the maleic anhydride.

The present invention additionally relates to a process for coproducing fumaric acid and maleic anhydride which comprises:

(a) deriving a composition comprising maleic anhydride and fumaric acid, from a system for the catalytic oxidation of butane or another hydrocarbon after dehydration;

(b) cooling said composition sufficiently to precipitate the fumaric acid;

(c) separating the fumaric acid precipitate from step (b) from the maleic anhydride, and recovering the fumaric acid;

(d) recovering the maleic anhydride and, optionally, distilling said maleic anhydride to obtain pure maleic anhydride and recovering the pure maleic anhydride; and (e) optionally, removing residual maleic anhydride from the recovered fumaric acid to obtain purified fumaric acid and then recovering the residual maleic anhydride.

The residual maleic anhydride is preferably removed from the fumaric acid to give purified fumaric acid with a stripping gas or by washing with water or another suitable solvent.

The present invention also relates to a process for coproducing fumaric acid and maleic anhydride which comprises:

(a) deriving a composition comprising molten maleic anhydride fumaric acid, and an entrainer, wherein a portion of the fumaric acid is dissolved in the maleic anhydride, from a system for the catalytic oxidation of butane or another hydrocarbon after dehydration;

(b) cooling said composition sufficiently to precipitate the fumaric acid;

(c) separating the fumaric acid precipitate from step (b) from the maleic anhydride/entrainer composition and, optionally, stripping the fumaric acid with a stripping gas to remove residual maleic anhydride, before recovering the fumaric acid;

(d) removing the entrainer from the from step (c) to produce a crude maleic anhydride product substantially free from said entrainer and, optionally, recovering the entrainer, and (e) distilling said crude maleic anhydride to obtain pure maleic anhydride and recovering the maleic anhydride.

The present invention further relates to a process which comprises:

(a) deriving a composition comprising molten maleic anhydride fumaric acid, and a xylene, wherein a portion of the fumaric acid is dissolved in the maleic anhydride, from a system for the catalytic oxidation of butane or another hydrocarbon after dehydration;

(b) cooling said composition sufficiently to precipitate the fumaric acid;

(c) separating the fumaric acid precipitate from step (b) from the maleic anhydride/entrainer composition by filtration and, optionally, stripping the fumaric acid with nitrogen to remove residual maleic anhydride before recovering the fumaric acid;

(d) removing the xylene from the maleic anhydride/entrainer composition from step (c) to produce a crude maleic anhydride product substantially free from said xylene and, optionally, recovering the xylene, and (e) optionally, distilling said crude maleic anhydride to obtain pure maleic anhydride and recovering the maleic anhydride.

In a preferred embodiment of the invention at least two filters are used to separate the fumaric acid precipitate and the filters are alternated so that FA precipitate is being collected on one filter while accumulated FA precipitate is removed from the other filter, cooled and sent to storage. In this way, the process can be kept running substantially continuously.

In an alternative embodiment, the entrainer can be removed by methods known to those skilled in the art prior to the fumaric acid recovery and the process carried out as described above but without the steps used to remove the entrainer.

In a preferred embodiment the separation of fumaric acid is conducted following dehydration in order to reduce fouling in the system; however, if desired, separation of fumaric acid may be conducted at any later point in the maleic anhydride production process, including following splitting in the splitting tower. When fouling of the system is not of concern, the separation may be conducted on the fumaric acid/maleic anhydride residue obtained from the fractionation tower.

BRIEF DESCRIPTION OF THE DRAWINGS

FIG. 4 illustrates a preferred filter assembly for use in the present invention.

DETAILED DESCRIPTION OF THE INVENTION

Figure 1:
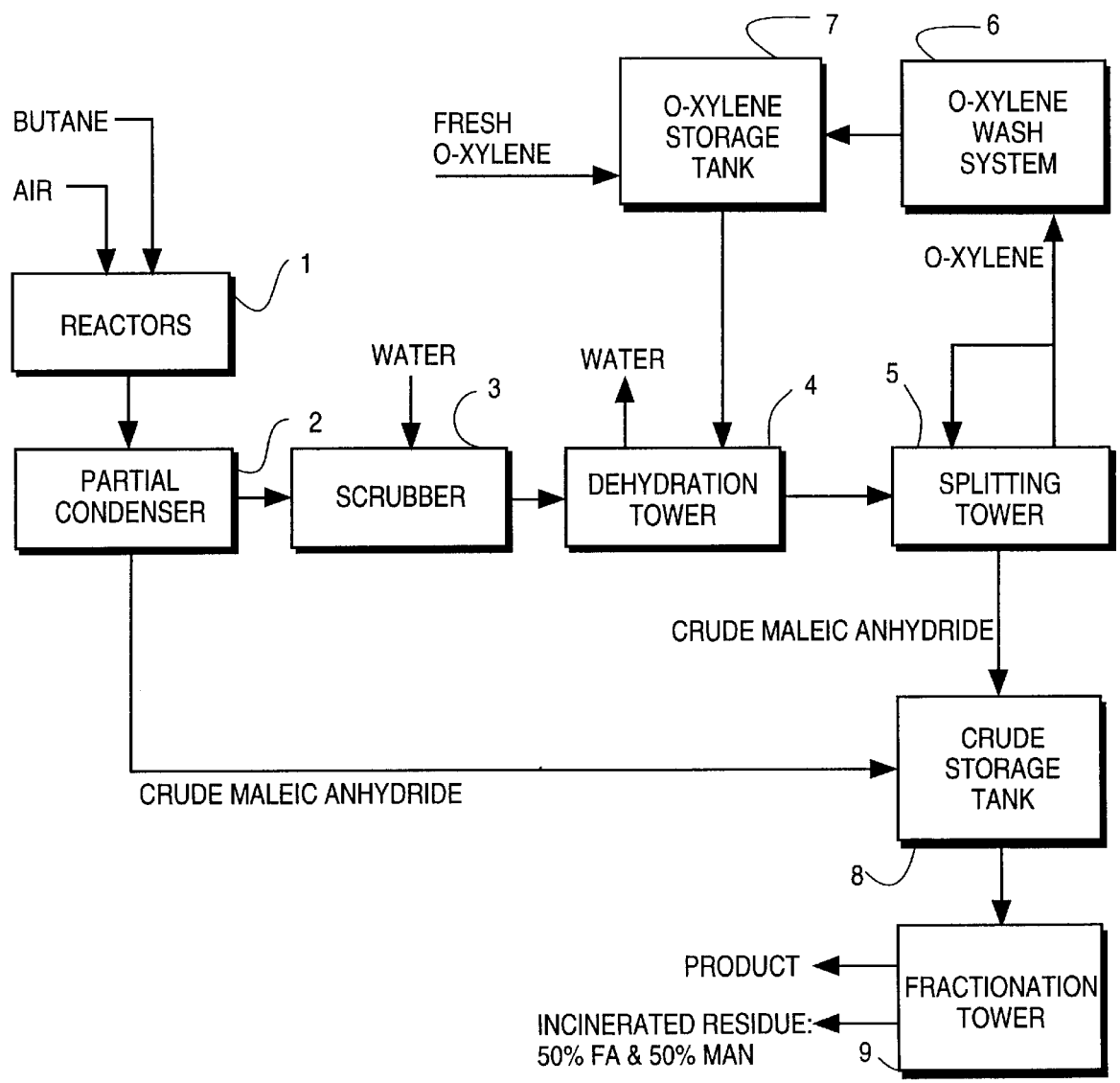
FIG. 1 illustrates a prior art process wherein a residue containing fumaric acid by-product and maleic anhydride is incinerated, and the fumaric acid is not recovered.

The present invention additionally relates to a process for coproducing fumaric acid and maleic anhydride which comprises:

(a) deriving a composition comprising molten maleic anhydride containing dissolved fumaric acid, from a system for the catalytic oxidation of butane or another hydrocarbon after dehydration;

(b) cooling said composition sufficiently to precipitate said fumaric acid;

(c) separating the fumaric acid precipitate from step (b) from the maleic anhydride, and recovering the fumaric acid; and (d) recovering the maleic anhydride.

The present invention likewise relates to a process for coproducing fumaric acid and maleic anhydride which comprises:

(a) deriving a composition comprising molten maleic anhydride containing dissolved fumaric acid, from a system for the catalytic oxidation of butane or another hydrocarbon after dehydration;

(b) cooling said composition sufficiently to precipitate said fumaric acid;

(c) separating the fumaric acid precipitate from step (b) from the maleic anhydride, and recovering the fumaric acid;

(d) recovering the maleic anhydride and, optionally, distilling said maleic anhydride to obtain pure maleic anhydride and recovering the pure maleic anhydride; and (e) optionally, removing residual maleic anhydride from the recovered fumaric acid to obtain purified fumaric acid and then recovering the residual maleic anhydride.

The residual maleic anhydride is preferably removed from the fumaric acid to give purified fumaric acid with a stripping gas or by washing with water or another suitable solvent.

The present invention also relates to a process for coproducing fumaric acid and maleic anhydride which comprises:

(a) deriving a composition comprising molten maleic anhydride containing an entrainer and dissolved fumaric acid, from a system for the catalytic oxidation of butane or another hydrocarbon after dehydration;

(b) cooling said composition sufficiently to precipitate said fumaric acid;

(c) separating the fumaric acid precipitate from step (b) from the maleic anhydride/entrainer composition and, optionally, stripping the fumaric acid with a stripping gas to remove residual maleic anhydride before recovering the fumaric acid;

(d) subjecting the maleic anhydride/entrainer composition from step (c) to column distillation to evaporate the entrainer to produce a crude maleic anhydride product substantially free from said entrainer and recovering the entrainer, and (e) recovering the crude maleic anhydride and, optionally, distilling said crude maleic anhydride to obtain pure maleic anhydride and recovering the pure maleic anhydride.

The present invention further relates to a process which comprises:

(a) deriving a composition comprising molten maleic anhydride containing an o-xylene entrainer and dissolved fumaric acid, from a system for the catalytic oxidation of butane or another hydrocarbon after dehydration;

(b) cooling said composition sufficiently to precipitate said fumaric acid;

(c) separating the fumaric acid precipitate from step (b) from the maleic anhydride/entrainer composition by filtration, stripping the fumaric acid with nitrogen to remove residual maleic anhydride, and recovering the fumaric acid;

(d) subjecting the maleic anhydride/o-xylene composition from step (c) to column distillation to evaporate the o-xylene and to produce a crude maleic anhydride product substantially free from said o-xylene and recovering the o-xylene, and (e) distilling said crude maleic anhydride to obtain pure maleic anhydride and recovering the pure maleic anhydride.

In a preferred embodiment of the invention at least two filters are used to separate the fumaric acid precipitate and the filters are alternated so that FA precipitate is being collected on one filter while accumulated FA precipitate is removed from the other filter, cooled and sent to storage. In this way, the process can be kept running substantially continuously.

In an alternative embodiment, the entrainer can be removed by methods known to those skilled in the art prior to the fumaric acid recovery and the process carried out as described above but without the steps used to remove the entrainer.

The present invention relates to a process for coproducing fumaric acid and maleic anhydride by filtering out FA formed as a by-product during the production of MAN and recovering it as a commercially useable product. The removal of the FA by means of the present process has the advantage of avoiding clogging of the equipment caused by precipitated FA and improving the economics of the MAN process by recovering MAN and FA that was incinerated to remove FA in earlier processes.

Fumaric acid solids, an unwanted by-product, are formed during the aqueous recovery of maleic anhydride in commercial processes. The FA solids have the consistency of sand, causing pump failure and plugging. As a result, the backend of the process periodically needs to be shut down for washout to remove the FA precipitate. The FA tends to settle in the bottoms of the final fractionator. In order to remove the FA solids from the bottom of the fractionation tower in previous processes, they were slurried 50/50 with the MAN product. This stream was then incinerated, which wasted about 2% of the MAN production and all of the FA. Removing the FA from the process produces an improvement in the process, reduces downtime, and provides a substantial economic benefit since both the recovered FA and the MAN which is recovered rather that incinerated have significant market value.

While the FA can be removed at the end of the process at the final fractionator, it is more advantageous to remove the FA where it is made, in the dehydration process, as in the preferred embodiment present invention. In a typical commercial MAN process, there may be many pumps, tanks, lines, and a xylene splitter tower between the dehydrator and the final fractionator where FA deposits can accumulate and cause fouling. By removing the fumaric acid upstream, maintenance and washout downtime is reduced. The recovered FA may be sold in the chemical market, producing an additional economic benefit.

In the process of the present invention the dehydrator bottoms stream from the dehydration step in MAN production which contains about 2 wt. % FA is filtered to remove the FA which can be collected from the filter and used commercially, optionally after further purification by washing with water. In a preferred embodiment, a slip stream of the dehydrator bottoms containing molten MAN, FA, and xylene at a temperature sufficient to contain solid FA will go the inside of a hollow, sintered metal filter where a FA cake will build up with time. Periodically, the flow to and from the filter will be switched off, and a purge of gas will blow MAN out of the filter cake. Then, the outlet gas flow will be closed which will allow the filter to pressurize to approximately 30 psig. A bottom discharge valve will open, at which point the FA cake will disengage from the filter because of the pressure difference and fall into a receiver. The disengaging process generally lasts only from a few seconds to a minute. The bottom valve is then closed and MAN/FA/xylene flow resumes. A bleed valve allows trapped gas to escape from the filter as the filter refills with MAN. The feed stream is generally at about 350° F. (176.7° C.).

Maleic anhydride, maleic acid, and fumaric acid are polyfunctional chemicals of significant commercial interest worldwide. They are chemically related in that each has $\alpha,\beta$ unsaturation associated with acid carbonyl functions. Maleic anhydride and maleic acid are industrially important raw materials in the manufacture of alkyd and polyester resins, surface coatings, lubricant additives, plasticizers, copolymers, and agricultural chemicals. Fumaric acid is used as a food acidulant and in the manufacture of unsaturated polyester resins, quick-setting inks, furniture lacquers and paper sizes.

Although maleic acid and fumaric acid are cis- trans-isomers, there are significant differences in their physical properties. For example, the melting point of FA is 287° C. (548.6° F.) (it starts to decompose at that temperature) whereas the melting point of MA is 130° C. (266° F.). FA is much less soluble in water, ethanol, and many other solvents than MA. The water solubility of FA is 0.7 wt. % whereas the water solubility of MA is 31.0 wt % This difference in solubility frequently causes problems when FA is formed as a by-product in the production of MA and/or MAN as the FA may precipitate out and cause clogging of the process equipment. The difference in solubility can however be used to separate FA when it is formed in a solution of MA. FA also has some solubility in hot MAN and this can be used to separate FA from reactor bottoms by pumping molten MAN containing FA to a cooling tank and cooling it to cause the FA to crystallize and precipitate out. The FA precipitate can then be separated and recovered. The process of the present invention provides a method of separating and recovering FA formed in the production of MAN so that both FA and MAN are recovered. The process has the advantages of yielding two commercially valuable products while at the same time reducing the equipment fouling, down time, and loss of product that occurs when the FA formed is just eliminated by incinerating it along with some of the MAN.

The process of the present invention relates to the production of MAN and FA, the separation of the FA from the process, and the finishing of MAN and FA as products. The process involves the production of MAN, the recovery of MAN as MA by contacting the reaction product stream with water, the production of FA from MA by providing the conditions that favor its formation, the separation of the FA, and the final recovery of MAN and FA.

FA is made by the thermal conversion of MA from the cis-isomer to the trans-isomer. MA is made by the reaction (hydration) of MAN. MAN+$H_2O$→MA. The physical properties of the two isomers, MA and FA are substantially different. The present process takes advantage of these differences to recover FA from an MA solution.

A stream from the reactors containing a dilute vapor of MAN is cooled sufficiently that a part of the MAN is condensed and recovered to give crude MAN which may contain small amounts of by-products and extraneous matter. The remaining MAN is recovered by contacting the vapor stream with water which converts the MAN to MA solution. This MA solution is then converted to MAN by removing the excess water and by dehydrating the MA to MAN by the application of heat. In the dehydration process, FA is made as a thermodynamically allowed phase. The FA is separated. The separation may be accomplished by any means for separating a solid from a suspension, for example, centrifugation or filtration. The crude MAN, the MAN produced in dehydration, and the FA may be further processed to remove impurities if desired.

In the process of the present invention, FA is generated by contacting MAN with water at temperature from about 127° F. (52.8° C.) to about 459° F. (237° C.) and preferably from about 300° F. (149° C.) to 375° F. (190.6° C.). Water is up to about 60% of the feed. The FA residence time is adjusted to control the concentration so that FA is in solution. The molten MAN and FA along with any entrainer go to a well-mixed tank where the temperature is lowered to from about 250° F. (121.2° C.) to about 300° F. (148.9° C.) by evaporative cooling. The tank contents are recycled by pumping material from the tank, separating and removing FA from the stream, and returning all of part of the substantially FA-free stream to the tank. The preferred way of recovering FA from the suspension of FA in liquid is by filtration. Any filter having a pore size suitable for separating the FA from solution and which can withstand the hot temperature and corrosive effects of the FA suspension may be used; however, a sintered metal filter is preferred. Other suitable filters include, but are not limited to, wound-metal filters, wire-mesh filters, porous glass and ceramic filters that are sintered or made of fibers or made of threads, and porous carbon filters. Filters made of plastics that can withstand both the temperature and the medium (molten MAN, FA, entrainer) may also be used in the present invention.

Optionally, some part of the FA-free stream may be diverted to another stage for processing the recovered MAN. The separated FA may be further processed to remove impurities if desired.

If further purification of the FA is desired, the crude, hot FA is stripped by contacting it with a stripping gas to remove absorbed material such as MAN. The stripping gas may be an inert gas such as nitrogen, carbon dioxide, argon, helium, combustion gases, etc. After it has been stripped, the FA is cooled, washed with water, and dried. Alternatively, the hot FA may be stripped with steam and cooled, or the unstripped FA containing residual MAN can be subjected to washing with water or another suitable solvent, such as alcohol, preferably methanol or ethanol, or acetone, to remove residual MAN and give a purified FA product. The MAN can then be recovered from the wash solvent by means known to those skilled in the art. If a centrifuge is used to recover the FA, the centrifuge cake containing FA and residual MAN can be subjected to such washing to purify FA and recover the residual MAN.

The residence time in the tank is determined by the volume of liquid held in the tank and the rate of feed to the tank. The residence time is preferably up to about 480 minutes or less with about 120 to about 240 minutes preferred.

The FA is formed by nucleation and crystal growth in a cooled tank. The residence time in the tank is controlled to give the preferred FA crystal size. It is desirable to have a crystal size which will provide FA which has a sand-like consistency. This enhances the ability to remove the FA from the filter by reverse flow through the filter (back flushing).

The design of the filter system depends on several variables. The filter size and flow rate are selected depending upon how much pressure drop is permitted, how long the filter cycle will be, and how thick the cake of FA will be. It may vary depending upon the type of filter used and the filter pore size. The filter flow rate should be such that the FA is filtered from the suspension without forcing the FA particles into the pores of the filter and causing it to become plugged.

For the present process, the rate of flow through the filter is preferably from about 0.01 up to about 1.82 gallons per minute (GPM) per square foot of filter area. A more preferred flow rate is up to about 0.52 GPM/sq. ft. and most preferred is from about 0.05 GPM/sq. ft. to about 0.3 GPM/sq. ft.

The filter cycle will depend upon the feed rate and the amount of FA solids in the feed. At the preferred feed rate the filter cycle time is at least about 30 minutes and the cake thickness is small so that the pressure drop is below 5 psig. This reduces the possibility of plugging the filter by forcing the FA particles into the pores of the filter.

In the production of MAN, butane or another hydrocarbon and air are reacted in the presence of a vanadium pentoxide (VPO) catalyst. The MAN which is formed comes out of the reactor in the vapor phase and this hot MAN gas is sent to a partial condenser where it is cooled. A portion of the MAN is condensed to a liquid and this crude liquid MAN is sent to a storage tank. The remaining MAN, which is still in the vapor phase and which also contains some nitrogen, oxygen, carbon dioxide, carbon monoxide, unconverted butane, water vapor and other trace components, is sent to a scrubber. Hot water is added to the scrubber, and the MAN vapor passes through it and reacts with the water and is converted to MA. For purposes of the present invention, the temperature of the water in the scrubber should be low enough to avoid converting the MA to FA as it is not desirable to make FA at this point in the process. A water temperature of up to about 180° F. (82.2° C.) or less is desirable. Preferably the water temperature in the scrubber is from about 140° F. (60° C.) to about 160° F. (71.1° C.) with about 160° F. more preferred. The conversion of MAN to MA in the scrubber typically results in a solution of from about 40 wt. % to about 70 wt. % MA in water, preferably from about 55% to about 60% maleic acid solution in water.

The temperature in the condenser is preferably from about 130° F. (54.4° C.) to about 145° F. (62.8° C.) with about 140° F. (60° C.) most preferred. Cooling the MAN vapor from the reactor typically results in the condensation of about 35 to about 40% of the MAN to a liquid. About 60 to about 65% of the MAN remains in the vapor state and is sent to the scrubber where it is converted to maleic acid.

The MA solution from the scrubber then goes to a dehydration tower where water is removed by azeotropic dehydration using an entrainer such as ortho-xylene. In the dehydration tower the MA solution is heated to a temperature that is sufficient to boil the MA solution but not so high as to cause degradation. A temperature of from about 300° F. (148.9° C.) up to about 375° F. (190.6° C.) can be used; however, preferably the temperature is less than 375° F. A temperature of from about 330° F. (165.6° C.) to about 360° F. (182.2° C.) is more preferred.

In a typical commercial MAN process the MAN/o-xylene composition goes to a splitting tower and crude MAN is separated and sent to a storage tank while the o-xylene is circulated to an o-xylene wash system where residual MAN is removed and recycled to the splitting tower while the washed o-xylene is returned to a storage tank and then recycled into the dehydration tower. The crude MAN in the storage tank goes to a fractionation tower and the MAN product is separated by distillation from lower and higher boiling materials. In previous maleic anhydride processes the fumaric acid which precipitated in the splitting tower, and the following parts of the system had to be washed out, mixed 50% FA/50% MAN and then incinerated. In the present process this is avoided by inserting a system to remove precipitated FA after the dehydration step in the process. This prevents fouling of the system with FA in the remainder of the process equipment. In the preferred process, a filtering system is inserted after the dehydration tower which filters out the fumaric acid precipitate and allows the FA to be collected, optionally purified by washing with water or another suitable solvent, and then used commercially.

The dehydration process results in the formation of some FA which precipitates and which can be removed by any means suitable for separating solids from liquids such as filtration or centrifugation, with filtration being preferable. The dehydrator bottoms stream can contain up to about 5 wt. % FA, up to about 4 wt. % o-xylene and up to about 98 wt. % MAN, and typically contains about 2 wt. % FA, about 2 wt. % o-xylene, and about 96% MAN. In the present process, a slip stream of molten MAN containing o-xylene and dissolved FA from the dehydrator, which has been cooled to a temperature sufficient to permit the FA to form a precipitate, is preferably passed through a filter allowing a cake of the FA precipitate to build up on the filter over time. Periodically, the flow to and from the filter may be switched off, and a purge of gas may be used to blow MAN off the FA filter cake. Then the outlet gas flow may be closed to allow the filter to pressurize to from about 15 psig to about 80 psig with about 30 psig preferred. The filter cake is then disengaged from the filter. For example, a bottom discharge valve may be opened causing the FA filter cake to disengage from the filter because of the pressure difference and fall into a receiver. Preferably, this disengaging process lasts from only a few seconds to about a minute. The bottom valve is then closed and MAN flow resumes. A bleed valve allows trapped gas to escape from the filter as the filter refills with MAN.

The FA which goes to the receiver may optionally be further purified by washing with water or another suitable solvent.

The following are typical processing conditions for a filter having a filter-area of 1.7 sq. ft. assuming a fumaric acid cake bulk-density of 62 lb/cu. ft.:

| | |
|---|---|
| Cake Thickness, inches. | 0.5 |
| FA Cake Wt., lb. | 4.39 |
| Filter Time, min. | 10 |
| MAN Feed rate, lb/min. | 22.0 |
| MAN Feed rate, cu.ft./min. | 0.272 |
| MAN Feed rate, gal/min. | 2.03 |
| Filter Time, min. | 20 |
| MAN Feed rate, lb/min | 11.0 |
| MAN Feed rate, cu.ft./min. | 0.136 |
| MAN Feed rate, gal/min | 1.02 |
| Filter Time, min. | 40 |
| MAN Feed rate, lb/min. | 5.5 |
| MAN Feed rate, cu.ft./min. | 0.068 |
| MAN Feed rate, gal/min. | 0.51 |

The feed stream for the above conditions is at about 350° F. (176.7° C.) and contains about 2 wt. % of fumaric acid solids. The typical fumaric acid particle size in this example is about 50 microns. The filter cake is wetted and held together with residual molten maleic anhydride. The residual MAN may be removed from the filtered FA by stripping with nitrogen or another suitable gas.

In one embodiment of the present invention, a flat filter may be used to collect the FA filter cake. Any filter having a pore size sufficient to filter out the FA and a composition sufficient to withstand the hot temperatures and corrosive environment may be used. A preferred filter is a hollow cylindrical sintered metal filter which may be obtained from Mott Metallurigical. Corp., Farmington, Conn. 06032-1489. In a preferred embodiment of the invention, the filter is a cylindrical sintered metal filter and the flow of the MAN/FA/o-xylene composition goes into the middle of the filter so that the MAN/o-xylene liquid comes out and the FA filter cake remains on the inside walls of the filter. The MAN/o-xylene is sent to a splitting tower where the o-xylene is removed, and the recovered crude MAN is sent to a storage tank. Optionally the crude MAN may be further purified by fractionation. The FA which collects on the inside walls of the filter is stripped of residual MAN with a gas such as nitrogen and then removed from the filter using back pressure. Due to the sand-like consistency of the FA, it readily detaches from the filter wall and is conveyed into a collection receptacle below the filter.

In a preferred embodiment of the invention, the fumaric acid precipitate is separated by passing the composition of molten maleic anhydride containing entrainer and fumaric acid obtained in step (b) through a filter assembly comprising a cylindrical filter element having one closed end, a hollow interior, and an inlet disposed opposite the closed end of the filter wherein said composition is fed, said filter being disposed within a housing having a solids receiving assembly attached thereto and disposed below the filter, an inlet port through which said composition is fed, and an outlet port through which the maleic anhydride/entrainer filtrate passes. Alternatively, the process can employ other filter configurations such as a cross-flow filter wherein the solids-laden stream passes continuously through a channel (open on both ends) made of porous material so that a part of the flow (molten MAN) passes through the porous material and the other part of the flow that contains the solids (FA) remains inside the channel. The result is to produce two streams—one that is more concentrated with regard to solids and another that is solids-free. The stream that contains the solids can be further separated in a second separation step to recover the FA.

Figure 2:
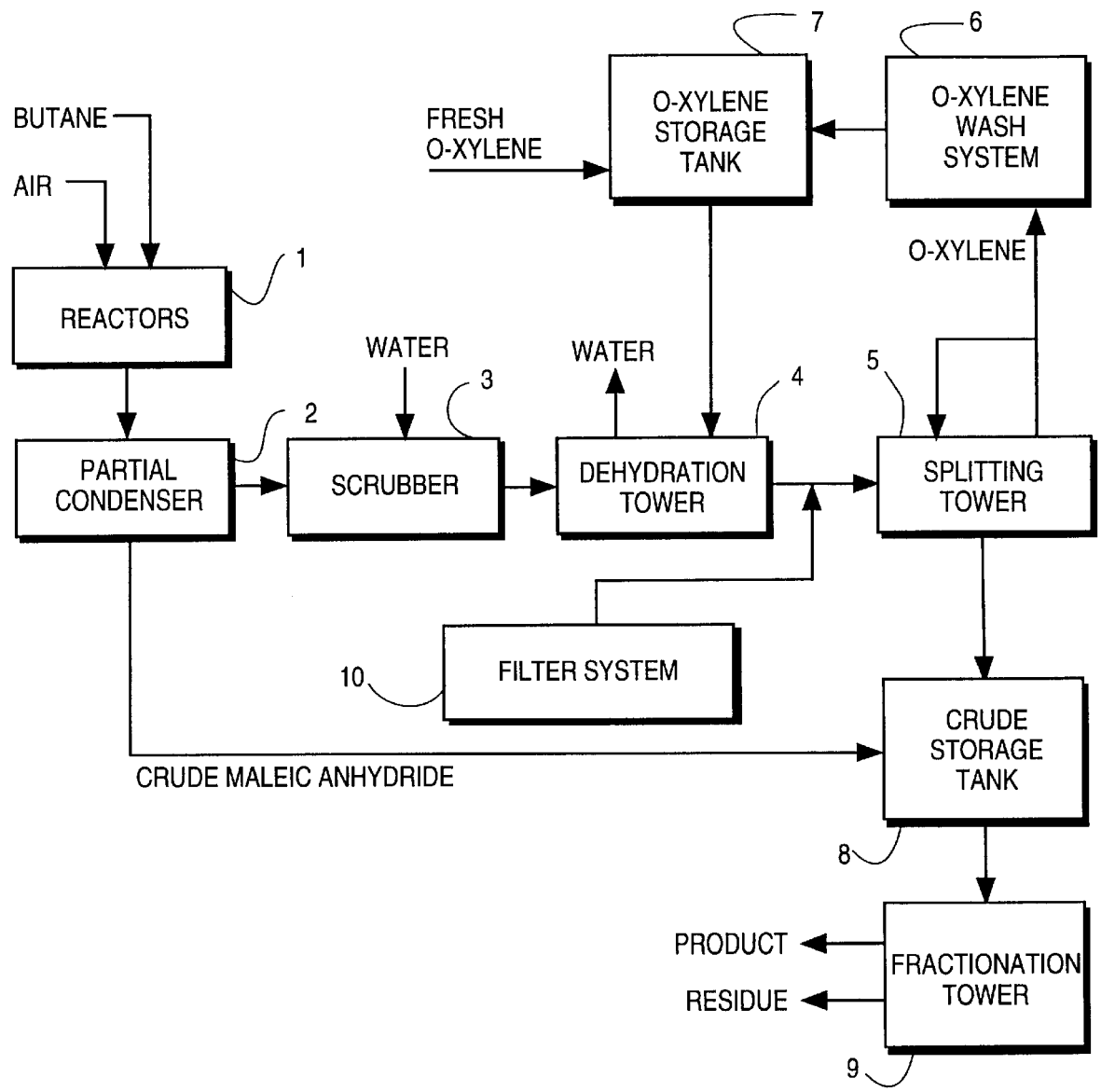
FIG. 2 illustrates a preferred embodiment of the present invention wherein a filter system (10) is used as the separator for recovering fumaric acid and is introduced between the dehydration tower (4) and the splitting tower (5).

In the embodiment of the process of the present invention shown in FIG. 2, butane or another hydrocarbon are oxidized in a reactor (1) using a VPO catalyst and MAN in the vapor phase comes out from the reactor as a gas. This MAN is introduced via a conduit to a partial condenser (2) where it is cooled sufficiently to condense part of the MAN vapor. Generally, from about 35 to about 40% of the vapor is condensed and then carried via a conduit to a crude storage tank (8). The temperature in the partial condenser can be from about 130° F. (54.4° C.) to about 145° F. (62.8° C.) with about 140° F. (60° C.) preferred. The uncondensed MAN which remains in the vapor phase and contains some nitrogen, oxygen, unreacted butane, $CO_2$ and CO is introduced via a conduit into a scrubber (3). Heated water is introduced into the scrubber via a conduit. It is desirable that the temperature of the water in the scrubber be low enough to avoid formation of fumaric acid. Preferably, the water temperature is up to about 180° F. In general, the preferred water temperature will range from about 140° F. to about 160° F. with about 160° F. being most preferred. In the scrubber the MAN vapor reacts with the water to form a maleic acid solution. Generally, a solution of from about 40 wt. % to about 70 wt. % of maleic acid in water is formed with about 55 wt. % to about 60 wt. % MA in water preferred.

The maleic acid solution from the scrubber is introduced into a dehydration tower (4) via a conduit. This may be a tray tower such as a conventional fractional distillation tower wherein heat is introduced at the bottom of the dehydration tower with cooling in the upper portion. An entrainer such as o-xylene is introduced into the dehydration tower via a conduit. The o-xylene acts to strip water away as the maleic acid solution is converted to maleic anhydride and water in the dehydration tower. The temperature in the dehydration step generally can be up to about 375° F. with less than 375° F. preferred. Preferably, the temperature will be from about 300° F. to about 375° F. with about 330° F. to about 360° F. preferred. The composition of the product from the dehydration step is generally about 96 wt. % MAN, about 2 wt. % FA, and about 2 wt. % o-xylene. This product is introduced via a conduit into a splitting tower (5) where o-xylene is removed by distillation and sent via a conduit to an o-xylene wash system (6) where it is washed to remove impurities and then sent via a conduit to an o-xylene storage tank (7) from which it may be recycled into the dehydration tower. The remaining MAN/FA is sent via a conduit to a crude storage tank (8) and then to a fractionation tower (9) for further purification.

Prior to the development of the process of the present invention, the FA in the product from the dehydration step has tended to cause fouling in the splitting tower, the crude MAN storage tank, the fractionation tower, and the interconnecting conduits, valves, etc. of the system necessitating periodic shutdowns for cleaning to flush out and remove the FA precipitate. Generally, the FA was disposed of by mixing it with MAN to produce a 50 wt. % FA:50 wt. % MAN composition which could then be incinerated. This was costly and time consuming and the incinerated FA and MAN were wasted. In the process of the present invention the FA and MAN which were previously incinerated are now recovered and can be used commercially.

The process of the present invention solves the problem of fouling of the production system with FA precipitate by removing the FA from the product of the dehydration step prior to sending the product to the splitting tower.

Figure 3:
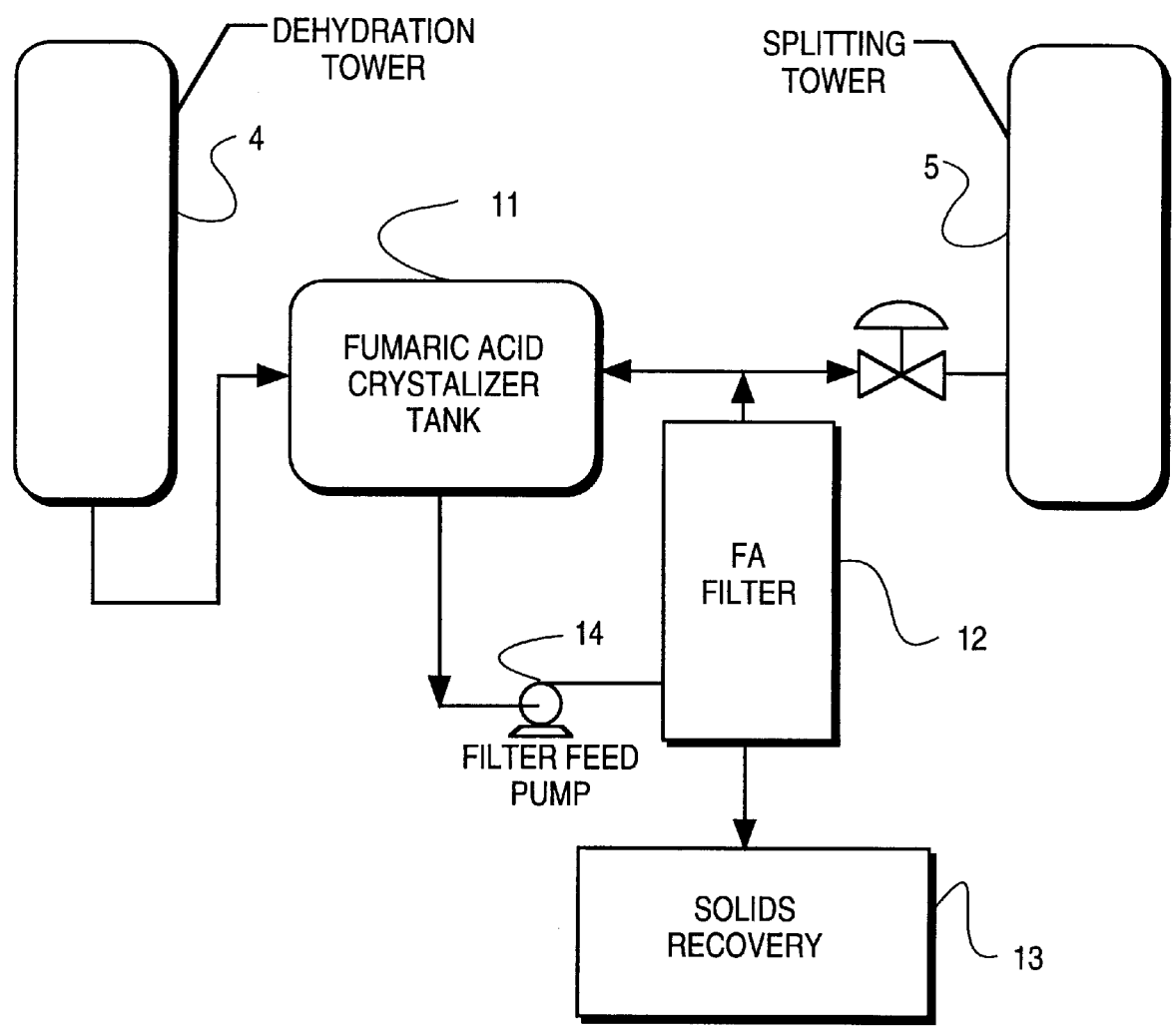
FIG. 3 illustrates a preferred filter system of the present invention.

In a preferred embodiment, a separation means (10) which is preferably a filter system is introduced between the dehydration tower (4) and the splitting tower (5) as shown in FIG. 2. Alternatively, a centrifuge or other separation means capable of separating the fumaric acid precipitate can be used. A preferred filter system is shown in FIG. 3. Using the process of the present invention the recovery efficiency for MAN is improved over that of earlier MAN processes, and the loss of MAN is reduced to about 1%.

In a alternative embodiment of the invention, the o-xylene or other entrainer may be removed prior to separation of the fumaric acid. In such embodiment, the separation means (10) would be located between the splitting tower (5) and the crude storage tank (8).

In another embodiment of the present system, when fouling of the system is not of concern, the separation of the fumaric acid can occur following fractionation and removal of the maleic anhydride product in the fractionation tower (9). In this embodiment the filter system is placed after the fractionation tower (9) and the FA/MAN residue (which comprises about 50% MAN and about 50% FA as shown in FIG. 1) is subjected to filtration to separate the FA. The separated FA and MAN can then be further purified as discussed above if desired.

In the filter system of FIG. 3, the MAN, FA; and o-xylene or other entrainer from the dehydration tower (4) is transported via a conduit to a crystallizing tank (11) where the material is cooled to a temperature in the range of about 260° F. (126.7° C.) to about 310° F. (154.4° C.) and more typically about 295° F. (146.1° C.) because the vacuum pressure evaporates the volatile MAN and organic components. The pressure in the tank is, at minimum, greater than the vapor pressure of MAN at its melting point (2.4 mm Hg at 127.1° F.). FA precipitates from solution as a solid because of the cooling.

From the crystallizing tank a slurry of FA in molten MAN with o-xylene is pumped via a pump (14) through the FA filter (12). The preferred filter is a hollow, cylindrical porous metal filter having a pore size of from about 0.2 microns to about 100 microns with a pore size of from about 2 microns to about 50 microns preferred, a pore size of about 2 microns to about 10 microns more preferred, and a pore size of about 5 microns most preferred. Preferably the filter is a sintered metal filter of 316 stainless steel. Filters suitable for practicing the present invention can be obtained from Mott Metallurgical Corp. Preferably more than one filter is used, and the filters are alternated so the process can be operated continuously. The FA slurry may be pumped through a first filter and the FA precipitate collected and then the pumped slurry may be switched to a second filter which continues to collect FA precipitate while the FA collected on the first filter is stripped with gas to remove MAN and then removed from the filter with back pressure and blown down and deposited in a solids recovery receptacle (13). The FA solids collecting on the filter do not cause a great build-up of pressure so a thick cake of FA can be built up on the filter walls. The FA solids come off the filter readily after being stripped to remove residual MAN and subjected to back pressure. Other solids separation devices such as centrifuges could also be used to remove the FA; however a filter has the advantage of providing a very high recovery of FA solids and facilitates stripping off residual MAN by passing a stripping gas through the FA filter solids while they are still on the filter. The stripping gas may be any gas that does not react with butane, carbon dioxide, or other combusted gases from the MAN process. Nitrogen is preferred, but argon and other inert gases which are well known to those skilled in the art could also be used. The greater the quantity of stripping gas used to remove the residual MAN, the lesser the amount of MAN that remains with the FA. However, higher quantities of stripping gas are required to remove low levels of MAN than high levels (diminishing returns). The optimum amount of stripping gas is determined by balancing the value of reducing the amount of MAN remaining on the FA against the cost of stripping gas. Up to about 100 standard cubic feet (SCF) of stripping gas per pound (lb) of FA solids are desirable. Up to about 32 SCF of stripping gas/lb of FA solids is preferred. Up to about 16 SCF of stripping gas/lb of FA solids is more preferred with less than 16 SCF of stripping gas/lb being most preferred.

The MAN/o-xylene filtrate is transported via a conduit to a stripping tower (5) where the o-xylene is removed. If desired, the o-xylene may be transported via a conduit into an o-xylene wash system, washed to purify it and then sent to a storage tank via a conduit and recycled to the dehydration tower.

In the filter system shown in FIG. 3, the MAN/FA/o-xylene effluent from the dehydration tower is introduced via a conduit into a cooling/crystallizer tank (11). The feed going into the crystallizing tank preferably contains about 2 wt. % FA and can contain from about 0.5 wt. % up to about 10 wt. % FA. In the cooling/crystallizing tank heat can be removed by any method; for example, by evaporative cooling, while the feed is mixed with an agitator. The temperature of the MAN/FA/o-xylene feed is reduced in the cooling tank to a temperature which will permit recovery of about 70% of the FA in the feed, which is preferably not more than 330° F. (165.6° C.). Preferably the temperature of the feed is cooled to from about 260° F.(126.7° C.) to about 315° F. (157.2° C.) by evaporative cooling. The pressure in the crystallizing tank may range from about 2.5 psig to about 11 psig with about 6 psig preferred. The feed is then pumped from the cooling tank into the FA filter (12). A portion of the MAN/o-xylene filtrate is recycled to the crystallizing tank and the remainder is sent via a conduit to the splitting tower (5). Preferably about 8% to about 50% and more preferably about 10% to about 25% of the MAN/o-xylene filtrate is recycled to the crystallizing tank. This pump-around recycling system has the advantage of helping to control the particle size of FA which goes to the filter by preventing growth of large crystals of FA on the walls of the crystallizing tank and encouraging formation of FA crystals in the crystallizing tank which are small and have a sand-like consistency. Large crystals, for example, about 1 mm in diameter, are less desirable as they are more likely to cause wearing of the metal filter. The crystal size is preferably greater than about 10 microns and less than about 1 mm. The pump flow is adjusted so that the residence time in the crystallizer tank is up to about 10 minutes with about 4 minutes to about 6 minutes preferred. The pumping capacity of the pump and the flow rate may vary depending on the size of the system and the filter. For the purposes of the present invention a flow rate of about 20 to about 110 gallons/minute(GPM) has been found to be useful with about 60 to about 105 GPM preferred. The discharge pressure from the crystallizing tank also depends upon the size of the system and the filter. A discharge pressure of from about 45 psig to about 55 psig is desirable. If desired, the amount of FA produced can be increased by introducing steam into the crystallizing tank.

Preferably the feed coming from the cooling/crystallizing tank is continuously pumped through the FA filter with part of the filtrate recycled to the cooling tank so that the pump used to pump the feed can be operated at high velocity. The pump must be able to generate a pressure sufficient to push the liquid through the filter. One skilled in the art can readily determine the pump capacity needed for a particular system.

In a preferred embodiment of the invention, the MAN/FA/o-xylene feed is pumped into a filter assembly such as that shown in FIG. 4. The filter assembly comprises a cylindrical filter (17) having a bottom inlet opening and a hollow interior (18) disposed within a housing (15). A solids receiving assembly (23) is disposed below the bottom of the filter and has an inlet port (16) through which a composition of MAN, FA and o-xylene is fed. Another port (24) is disposed at the bottom of the solids receiving assembly through which stripping gas may be fed. A port (21) through which a blowdown gas may be fed is disposed near the top of the filter housing. Another port (20) through which the MAN/o-xylene filtrate is fed is disposed near the top of the filter housing opposite the blowdown gas port (21). A port (22) through which the blowdown gas exits is disposed on the filter housing at a point below the blowdown gas entry port (21).

During filtration, a MAN/FA/o-xylene composition (or MAN/FA composition, if the o-xylene entrainer has been removed prior to this step) is fed through the port (16) and is forced up through the filter (17). The FA precipitate accumulates on the interior walls of the filter (25) and the MAN/o-xylene filtrate passes through the filter and is pumped out the filtrate exit port (20). The feed from the crystallizer tank is passed through the filter until the filter is full or until a delta pressure between the feed inlet (16) to the filter and the filtrate discharge port (20) has reached the desired level which is typically up to about 30 psig or less. A delta pressure of less than 30 psig is preferred. During this time, ports 21, 22 and 24 are shut. FA has been accumulated on the filter, the feed is shut off, and a stripping gas such as nitrogen is fed into the filter assembly through the port 24. The stripping gas forces the remainder of the filtrate out of the filter assembly and strips residual MAN from the filter cake. The FA accumulated on the filter cake consists of FA with absorbed MAN. The MAN is a solid at temperatures below about 127° F. (52.8° C.) and a liquid above that temperature. The temperature of the blowdown gas is preferably at least about 130° F. (54.4° C.). The filtrate exit port is then closed and blowdown gas is fed in through port 21. It pressurizes the filter to 15 psig. to 60 psig. The FA, which has a sand-like quality, falls into the solids receiving assembly (23) and from there it is passed through port 24 into a FA storage container when the pressure is released through a valve at port 24. The FA product recovered is at a temperature of about 130° F. (54.4° C.) and is cooled to about 100° F. (37.8° C.) and stored for further processing. The recovered FA may be used as is, or may be further purified by washing with water or another suitable solvent which does not dissolve FA such as alcohol or acetone, or may be recrystallized from dimethyl sulfoxide (DMSO).

Alternatively, If the filter cake is not stripped with a stripping gas, the filter cake can be removed from the filter with a liquid, for example, by reversing the filtrate flow long enough to disengage the filter cake from the wall of the filter. The filter cake containing residual maleic anhydride can then be removed from the filter and the filtering process can be resumed.

If one wishes to obtain greater amounts of fumaric acid product, the process configuration that is described above readily allows ways for the FA to be increased if desired. The amount of FA product can be increased by the following methods:

(a) steam can be injected into the MAN/FA stream ahead of the separator to increase the amount of FA. Steam temperatures higher than 310° F. (154.4° C.) are preferred (MAN and water combine to make either maleic acid or fumaric acid. Higher temperatures increase the rate of conversion to FA);

(b) water can be injected into the MAN/FA stream ahead of the separator. However, if water is injected, the process must accommodate the consequences, I. e., it must allow for the vapor expansion of the water and provide heat because the composition will cool when the water boils or the composition must be pressurized to keep the water in the liquid state;

(c) prior to recycling MAN filtrate to a cooling apparatus. (this can be a tank or other container that is held under vacuum so that evaporation cools the composition) water or steam can be injected to increase the amount of FA; and (d) instead of stripping gas, steam or water can be injected into the separated FA, which has residual MAN, to convert the residual MAN to FA.

If making additional FA is practiced, the composition of the stream (FA in MAN composition) would include a composition that is comprised of FA, MAN, and, possibly, entrainer or other material. The composition of the stream would preferably comprise up to about 20% FA, up to about 80% MAN, and up to about 4% entrainer and other material.

The examples which follow illustrate the invention in more detail. The following Examples will serve to illustrate certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

EXAMPLE 1

A slurry containing 2% FA was filtered using Mott Metallurgical HyPulse® filters which may be obtained from Mott Metallurgical Corp. The filters had a pore size of 5 microns. The filtering proceeded well; thick (up to 3 inch) FA filter cakes were generated, which showed a maximum 7 psi pressure drop to flow. The filter cakes disengaged from the filter element substantially intact using a backflush of nitrogen at 30 psig. Analysis of the filter cakes showed low (5%) residual maleic anhydride.

EXAMPLE 2

A stainless steel cylinder filter 2 inches in diameter and 13 inches long was purchased from Mott Metallurgical Corp. A MAN production unit was assembled incorporating a five-gallon heated feed tank hooked up to a centrifugal pump. All associated lines and the filter were heat traced. Qualitative tests were performed using a 5 micron filter element on simulated feed (2% fumaric acid in maleic anhydride). The feed temperature was maintained in the range of 150° F. (65.6° C.) to 200° F. (193.3° C.). The feed tank, which was at atmospheric pressure, normally held about 5 gallons of feed material. The discharge pressure of the pump was 60 psig. The filtrate receiver was at atmospheric pressure.

The tests proceeded rapidly, taking only about 1 minute to empty the feed tank. After filtering, residual MAN absorbed on the FA solids was removed by stripping. A nitrogen strip gas was engaged at about 100 standard cubic feet per hour (scfh) for 5 minutes. The filter housing was pressurized to 30 psig, and the FA cake was disengaged through a bottom drain valve. The filter remained very clean, and the cake had a minimum of residual maleic anhydride in it. The speed at which the FA was filtered and the amount filtered made it possible to use the full capacity of the filter and to completely fill the filter with solids for each run. Quantitative tests were performed to optimize run length and the necessary stripping time. The percentage of MAN on the filter cakes was analyzed by liquid chromatography. The experimental system may be useful for other processes besides MAN. Table 1 gives dimensions and typical operating conditions for the Example 2 filter.

TABLE 1

| Filter Dimensions | |
| --- | --- |
| ID* of filter element | 1 ⅞ inches |
| Length of filter element | 13 inches |
| ID of filter housing | 2 ¾ inches |
| Length of filter housing | 19 inches |
| Filter micron size | 5 microns |
| Material of construction | 316 Stainless steel |
| *Internal Diameter | |
| Filter Operating Conditions | |
| Flow rate | 4 gallons per minute (GPM) |
| Percent solids in feed | 1–2% |
| Amount of solids filtered | 95% |
| Length of filter cycle | 1 minute |
| Length of stripping cycle | 5 minutes |
| Pressure of stripping gas | 40 psig |

TABLE 1-continued

| | |
| --- | --- |
| Flow rate of stripping gas | 100 scfh |
| Pressure of filter prior to blowdown | 40 psig |
| Residual MAN on filter cake | 5–10% |

EXAMPLE 3

A larger sintered metal filter was purchased from Mott Metallurgical Corp. This filter was 4 inches in diameter and 10 feet long. The filter unit was placed at the desired location in a pilot plant scale of the MAN process between the dehydration tower and the splitting tower. The time required to fill the filter with solids was 8 minutes. After stripping the FA filter cake for 5 minutes with nitrogen, th cake was dumped into a receiving container. The solids looked clean and dry. Table 2 gives dimensions and typical operating conditions for the Example 3 filter as well a the composition of the FA filter cake.

TABLE 2

| Filter Dimensions | |
| --- | --- |
| ID* of filter element | 2.5 inches |
| Length of filter element | 48 inches |
| ID of filter housing | 4 inches |
| Length of filter housing | 74 inches |
| Filter micron size | 5 microns |
| Material of construction | 316 Stainless steel |
| *Internal Diameter | |
| Filter Operating Conditions | |
| Flow rate | 4 gallons per minute (GPM) |
| Percent solids in feed | 1–2% |
| Amount of solids filtered | 95% |
| Length of filter cycle | 8–20 minutes |
| Length of stripping cycle | 5 minutes |
| Pressure of stripping gas | 60 psig |
| Flow rate of stripping gas | 240 scfh |
| Pressure of filter prior to blowdown | 60 psig |
| Residual MAN on filter cake | 5–10% |
| Feed temperature | 300° F. (148.9° C.) |
| Composition of Fumaric Acid Filter Cake | |
| Fumaric acid, Wt. % | 92.1 |
| Maleic acid, Wt. % | 0.2 |
| Maleic Anhydride, Wt. % | 7.9 |
| Water | ND |
| Organic Solvent, wppm | 30 |
| Bulk Density g/cc | 0.75 |
| Particle Size, microns | |
| 10 Vol. % is Below | 93 |
| Median, 50 Vol. % is Below | 275 |
| 90 Vol. % is Below | 550 |
| Average Size | 297 |

EXAMPLE 4

Three tests were completed on a mixture of about 96.4 wt. % MAN, 2 wt. % FA, 2% o-xylene which originated from the dehydration step of a MAN production process. A stream was taken from the FA crystallizer discharge pump and put through the filter. Filtering duration was 10 minutes, and the recovered FA was about 1.5 to about 1.8 wt. % of the feed. Residual MAN on the FA cake was measured in the range of 8 to 13% and this decreases with increased stripping time. The filtered FA had an average particle size of 297 microns which reflects the growth of the crystals in the FA crystallizer tank. The fumaric acid solids obtained had a yellow-white appearance. They were very pure and had low levels of contaminants. Results are shown in Table 3.

TABLE 3

| Run | Total Feed rate, lb/min | Feed Time min. | Strip Time min. | Strip Rate scfh | Temp °F. | Delta P, psig | Wt. Solids lbs. |
|---|---|---|---|---|---|---|---|
| 1 | 39.6 | 10 | 2 | 32 | 280 | 10 | 7 |
| 2 | 39.6 | 10 | 4 | 32 | 300 | 26.5 | 5.90 |
| 3 | 36.9 | 10 | 16 | 32 | 298 | 18 | 5.55 |

That which is claimed is:

1. A process for coproducing purified fumaric acid and maleic anhydride which comprises:
   (a) deriving a composition comprising molten maleic anhydride and fumaric acid, from a system for the catalytic oxidation of butane or another hydrocarbon by:
      (1) deriving a stream comprising vapor phase MAN from a system for the catalytic oxidation of butane or another hydrocarbon;
      (2) condensing a portion of said maleic anhydride vapor and separating crude maleic anhydride thus formed from uncondensed maleic anhydride vapor;
      (3) deriving an aqueous solution of maleic acid by adding water to the uncondensed maleic anhydride vapor at a temperature sufficient to form maleic acid without forming fumaric acid;
      (4) dehydrating the maleic acid solution and recovering a crude maleic anhydride stream and a dehydrator bottoms stream comprising molten maleic anhydride and fumaric acid;
   (b) cooling the dehydrator bottoms stream comprising molten maleic anhydride and fumaric acid to a temperature sufficient to precipitate the fumaric acid;
   (c) separating the fumaric acid precipitate from step (b) from the molten maleic anhydride, removing residual maleic anhydride from the fumaric acid precipitate, and recovering purified fumaric acid; and
   (d) distilling the crude maleic anhydride stream obtained in step (a)(4) and the crude maleic anhydride obtained in step (a)(2) to obtain pure maleic anhydride.

2. A process according to claim 1 for coproducing purified fumaric acid and maleic anhydride which comprises:
   (a) deriving a composition comprising molten maleic anhydride and fumaric acid, from a system for the catalytic oxidation of butane or another hydrocarbon by:
      (1) deriving a stream comprising vapor phase MAN from a system for the catalytic oxidation of butane or another hydrocarbon;
      (2) condensing a portion of said maleic anhydride vapor and separating crude maleic anhydride thus formed from uncondensed maleic anhydride vapor;
      (3) forming an aqueous solution comprising about 40 to about 70 weight percent maleic acid by adding water to the uncondensed maleic anhydride vapor at a temperature of about 140° F. to about 180° F.;
      (4) dehydrating the maleic acid solution at a temperature of about 300° F. to about 375° F. and recovering a crude maleic anhydride stream and a dehydrator bottoms stream comprising molten maleic anhydride and fumaric acid;
   (b) cooling said dehydrator bottom stream comprising molten maleic anhydride and fumaric acid to a temperature of about 250° F. to about 330° F. to precipitate the fumaric acid and form a slurry of fumaric acid in molten maleic acid;
   (c) separating the fumaric acid precipitate from the molten maleic anhydride, stripping the fumaric acid to remove residual maleic anhydride, and recovering purified fumaric acid; and
   (d) distilling the crude maleic anhydride stream obtained in step (a)(4) and the crude maleic anhydride obtained in step (a)(2) to obtain pure maleic anhydride.

3. The process of claim 2 wherein the cooling in step (b) is conducted at a pressure of about 2.5 psig to about 11 psig.

4. The process of claim 2 wherein the residual maleic anhydride stripped from the fumaric acid precipitate in step (c) is recovered and distilled to form pure maleic anhydride.

5. The process of claim 2 wherein the dehydration in step (a)(4) is conducted at a temperature of about 330° F. to about 360° F., wherein water is added to uncondensed maleic anhydride vapor in step (a)(3) at a temperature of about 140° F. to about 160° F., and wherein the fumaric acid precipitation in step (b) is conducted at a temperature of about 250° F. to about 300° F.

6. A process according to claim 1 for coproducing purified fumaric acid and maleic anhydride which comprises:
   (a) deriving a composition comprising molten maleic anhydride and fumaric acid, from a system for the catalytic oxidation of butane or another hydrocarbon by:
      (1) deriving a stream comprising vapor phase MAN from a system for the catalytic oxidation of butane or another hydrocarbon;
      (2) condensing a portion of said maleic anhydride vapor and separating crude maleic anhydride thus formed from uncondensed maleic anhydride vapor;
      (3) deriving an aqueous solution of maleic acid by adding water to the uncondensed maleic anhydride vapor at a temperature sufficient to form maleic acid without forming fumaric acid;
      (4) dehydrating said maleic acid solution in the presence of an entrainer and recovering a stream comprising crude maleic anhydride and entrainer and a dehydrator bottoms stream comprising molten maleic anhydride, entrainer, and fumaric acid;
   (b) cooling the dehydrator bottoms stream comprising molten maleic anhydride, entrainer, and fumaric acid to a temperature sufficient to precipitate the fumaric acid;
   (c) separating the fumaric acid precipitate from step (b) from the molten maleic anhydride and entrainer, removing residual maleic anhydride and entrainer from the fumaric acid, and recovering purified fumaric acid; and
   (d) splitting the crude maleic anhydride/entrainer stream obtained in step (a)(4) to remove the entrainer and distilling the resulting crude maleic anhydride and the crude maleic anhydride obtained in step (a)(2) to obtain pure maleic anhydride.

7. A process according to claim 6 for coproducing purified fumaric acid and maleic anhydride which comprises:
   (a) deriving a composition comprising molten maleic anhydride and fumaric acid, from a system for the catalytic oxidation of butane or another hydrocarbon by:
      (1) deriving a stream comprising vapor phase MAN from a system for the catalytic oxidation of butane or another hydrocarbon;
      (2) condensing a portion of said maleic anhydride vapor and separating crude maleic anhydride thus formed from uncondensed maleic anhydride vapor;
      (3) forming an aqueous solution comprising about 40 to about 70 weight percent maleic acid by adding water to the uncondensed maleic anhydride vapor at a temperature of about 140° F. to about 180° F.;

(4) dehydrating the maleic acid solution in the presence of an entrainer at a temperature of about 300° F. to about 375° F. and recovering a stream comprising crude maleic anhydride and entrainer and a dehydrator bottoms stream comprising molten maleic anhydride, up to about 4 weight percent entrainer, and fumaric acid;

(b) cooling the dehydrator bottoms stream comprising molten maleic anhydride, entrainer, and fumaric acid to a temperature of about 250° F. to about 310° F. to precipitate the fumaric acid and form a slurry of fumaric acid in molten maleic anhydride and entrainer;

(c) separating the fumaric acid precipitate from the molten maleic anhydride and entrainer, stripping the fumaric acid to remove residual maleic anhydride and entrainer, and recovering purified fumaric acid; and (d) splitting the crude maleic anhydride/entrainer stream obtained in step (a)(4) to remove the entrainer and distilling the resulting crude maleic anhydride and the crude maleic anhydride obtained in step (a)(2) to obtain pure maleic anhydride.

8. The process of claim 6 wherein the dehydrator bottoms stream obtained in step (a)(4) following dehydration comprises molten maleic anhydride, up to about 4 weight percent entrainer, and about 0.5 to about 10 weight percent fumaric acid.

9. The process of claim 7 wherein the entrainer is o-xylene, and the composition obtained in step (a)(4) following dehydration comprises about 96 weight percent molten maleic anhydride, about 2 weight percent o-xylene, and about 2 weight percent fumaric acid.

10. The process of claim 7 wherein the dehydrator bottoms stream obtained in step (a)(4) following dehydration comprises molten maleic anhydride, up to about 4 weight percent entrainer, and about 0.5 to about 10 weight percent fumaric acid, and wherein the particle size of the fumaric acid precipitate formed in step (b) is from about 10 microns to about 1 mm.

11. The process of claim 10 wherein the particle size of the fumaric acid precipitate is from about 10 microns to about 550 microns.

12. The process of claim 7 wherein the aqueous solution of maleic acid obtained in step (a)(3) comprises about 50 to about 60 weight percent maleic acid.

13. A process according to claim 7 for coproducing purified fumaric acid and maleic anhydride which comprises:

(a) deriving a composition comprising molten maleic anhydride and fumaric acid, from a system for the catalytic oxidation of butane or another hydrocarbon by:

(1) deriving a stream comprising vapor phase MAN from a system for the catalytic oxidation of butane or another hydrocarbon;

(2) condensing a portion of said maleic anhydride vapor and separating crude maleic anhydride thus formed from uncondensed maleic anhydride vapor;

(3) forming an aqueous solution comprising about 40 to about 70 weight percent maleic acid by adding water to the uncondensed maleic anhydride vapor at a temperature of about 140° F. to about 180° F.;

(4) dehydrating the maleic acid solution in the presence of an entrainer at a temperature of about 300° F. to about 375° F. and recovering a stream comprising crude maleic anhydride and entrainer and a dehydrator bottoms stream comprising molten maleic anhydride, up to about 4 weight percent entrainer, and fumaric acid;

(b) cooling the dehydrator bottoms stream comprising molten maleic anhydride, entrainer, and fumaric acid to a temperature of about 250° F. to about 310° F. to precipitate the fumaric acid and form a slurry of fumaric acid in molten maleic acid and entrainer;

(c) separating the fumaric acid precipitate from the molten maleic anhydride and entrainer, adding steam or hot water to the fumaric acid precipitate to convert residual maleic anhydride to fumaric acid, and recovering purified fumaric acid; and (d) splitting the crude maleic anhydride/entrainer stream obtained in step (a)(4) to remove the entrainer and distilling the resulting crude maleic anhydride and the crude maleic anhydride obtained in step (a)(2) to obtain pure maleic anhydride.

14. A process according to claim 13 for coproducing purified fumaric acid and maleic anhydride which comprises:

(a) deriving a composition comprising molten maleic anhydride and fumaric acid, from a system for the catalytic oxidation of butane or another hydrocarbon by:

(1) deriving a stream comprising vapor phase MAN from a system for the catalytic oxidation of butane or another hydrocarbon;

(2) condensing a portion of said maleic anhydride vapor and separating crude maleic anhydride thus formed from uncondensed maleic anhydride vapor;

(3) forming an aqueous solution comprising about 50 to about 60 weight percent maleic acid by adding water to the uncondensed maleic anhydride vapor at a temperature of about 140° F. to about 160° F.;

(4) dehydrating the maleic acid solution in the presence of an entrainer at a temperature of about 330° F. to about 360° F. and recovering a stream comprising crude maleic anhydride and entrainer and a dehydrator bottoms stream comprising molten maleic anhydride, up to about 4 weight percent entrainer, and fumaric acid;

(b) adding water to the dehydrator bottoms stream to convert a portion of the maleic anhydride to fumaric acid and then cooling the dehydrator bottoms stream comprising molten maleic anhydride, entrainer, and fumaric acid to a temperature of about 250° F. to about 310° F. to precipitate the fumaric acid and form a slurry of fumaric acid in molten maleic acid;

(c) separating the fumaric acid precipitate from the molten maleic anhydride and entrainer, stripping the fumaric acid to remove residual maleic anhydride and entrainer, and recovering purified fumaric acid; and (d) splitting the crude maleic anhydride/entrainer stream obtained in step (a)(4) to remove the entrainer and distilling the resulting crude maleic anhydride and the crude maleic anhydride obtained in step (a)(2) to obtain pure maleic anhydride.

15. A process according to claim 13 for coproducing purified fumaric acid and maleic anhydride which comprises:

(a) deriving a composition comprising molten maleic anhydride and fumaric acid, from a system for the catalytic oxidation of butane or another hydrocarbon by:

(1) deriving a stream comprising vapor phase MAN from a system for the catalytic oxidation of butane or another hydrocarbon;

(2) condensing a portion of said maleic anhydride vapor and separating crude maleic anhydride thus formed from uncondensed maleic anhydride vapor;

(3) forming an aqueous solution comprising about 50 to about 60 weight percent maleic acid by adding water to the uncondensed maleic anhydride vapor at a temperature of about 140° F. to about 160° F.;

(4) dehydrating the maleic acid solution in the presence of an entrainer at a temperature of about 330° F. to about 360° F. and recovering a stream comprising crude maleic anhydride and entrainer and a dehydrator bottoms stream comprising molten maleic anhydride, up to about 4 weight percent entrainer, and fumaric acid;

(b) adding water to the dehydrator bottoms stream to convert a portion of the maleic anhydride to fumaric acid and then cooling the dehydrator bottoms stream comprising molten maleic anhydride, entrainer, and fumaric acid to a temperature of about 250° F. to about 310° F. to precipitate the fumaric acid and form a slurry of fumaric acid in molten maleic acid;

(c) separating the fumaric acid precipitate from the molten maleic anhydride and entrainer, adding steam or hot water to the fumaric acid precipitate to convert residual maleic anhydride to fumaric acid, and recovering purified fumaric acid; and (d) splitting the crude maleic anhydride/entrainer stream obtained in step (a)(4) to remove the entrainer and distilling the resulting crude maleic anhydride and the crude maleic anhydride obtained in step (a)(2) to obtain pure maleic anhydride.

16. The process of claim 6 wherein the entrainer is selected from o-xylene, p-xylene, m-xylene, and pseudocumene or mixtures thereof.

17. The process of claim 16 wherein the entrainer is o-xylene.

18. The process of claim 7 wherein the entrainer is selected from o-xylene, p-xylene, m-xylene, and pseudocumene or mixtures thereof.

19. The process of claim 18 wherein the entrainer is o-xylene.

20. A process according to claim 1 wherein the fumaric acid precipitate is separated by filtration.

21. A process according to claim 1 wherein the fumaric acid precipitate is separated by centrifugation.

22. A process according to claim 20 wherein the fumaric acid precipitate is separated by filtration using at least two filters wherein said filters are alternated to provide continuous operation of the process.

23. A process according to claim 6 wherein the dehydrator bottoms stream obtained in step (a)(4) comprises up to about 5 weight percent fumaric acid, up to about 4 weight percent entrainer, and up to about 98 weight percent maleic anhydride.

24. A process according to claim 23 wherein the dehydrator bottoms stream obtained in step (a)(4) comprises up to about 2 weight percent fumaric acid, up to about 2 weight percent entrainer, and up to about 96 weight percent maleic anhydride.

25. A process according to claim 1 wherein the composition is cooled to a temperature of about 260° F. to about 310° F. in step (b).

26. A process according to claim 20 wherein the fumaric acid precipitate is separated by filtration with a filter having a pore size of from about 0.02 to about 100 microns.

27. A process according to claim 20 wherein said filter is a sintered metal filter.

28. A process according to claim 20 wherein said filter has a pore size of from about 2 microns to about 50 microns.

29. A process according to claim 20 wherein said filter has a pore size of from about 2 microns to about 10 microns.

30. A process according to claim 20 wherein said filter has a pore size of about 5 microns.

31. A process according to claim 7 wherein about 8 weight percent to abut 50 weight percent of the maleic anhydride/entrainer separated from the fumaric acid precipitate in step (c) is recycled to a cooling apparatus and mixed with the dehydrator bottoms stream comprising molten maleic anhydride, entrainer and fumaric acid obtained in step (a)(4).

32. A process according to claim 7 wherein the fumaric acid precipitate is separated by passing the slurry of fumaric acid in molten maleic anhydride and entrainer obtained in step (b) through a filter assembly comprising a cylindrical filter element having one closed end, a hollow interior, and an inlet disposed opposite the closed end of the filter wherein said composition is fed, said filter being disposed within a housing having a solids receiving assembly attached thereto and disposed below the filter, an inlet port through which said composition is fed, and an outlet port through which the maleic anhydride/entrainer filtrate passes.

33. A process according to claim 32 wherein said filter housing further has a second inlet port through which blowdown gas is passed to remove the filtered fumaric acid from the filter, a second outlet port disposed below said second inlet port through which the blowdown gas can exit the filter housing, and a third inlet port disposed below said filter through which said stripping gas is passed.

34. A processing according to claim 32 wherein said filter has a pore size of about 0.2 microns to about 100 microns.

35. A process according to claim 1 wherein the recovered fumaric acid is further purified by washing with water or another solvent.

36. A process according to claim 20 wherein said filter is selected from sintered metal filters, wound-metal filters, wire-mesh filters, porous glass filters, ceramic filters, and plastic filters.

37. A process according to claim 1 wherein the fumaric acid concentration in the maleic anhydride/fumaric acid composition is increased by adding steam to the maleic anhydride/fumaric acid composition prior to precipitation of the fumaric acid.

38. A process according to claim 1 wherein the fumaric acid concentration in the maleic anhydride/fumaric acid composition is increased by adding water to the maleic anhydride/fumaric acid composition prior to precipitation of the fumaric acid.

39. The process of claim 36 wherein the filter is a sintered metal filter having a pore size of about 0.2 microns to about 100 microns.

40. The process of claim 39 wherein the filter is a sintered stainless steel filter having a pore size of about 2 to about 100 microns.

41. The process of claim 37 wherein a maleic anhydride/fumaric acid composition comprising up to about 80 weight percent maleic anhydride and up to about 20 weight percent fumaric acid is obtained following the addition of steam.

42. The process of claim 38 wherein a maleic anhydride/fumaric acid composition comprising up to about 80 weight percent maleic anhydride and up to about 20 weight percent fumaric acid is obtained following the addition of water.

43. A process according to claim 6 wherein the fumaric acid precipitate is separated by filtration with a filter selected from sintered metal filters, wound-metal filters, wire-mesh filters, porous glass filters, ceramic filters, and plastic filters.

44. A process according to claim 7 wherein the fumaric acid precipitate is separated by filtration with a filter selected from sintered metal filters, wound-metal filters, wire-mesh filters, porous glass filters, ceramic filters, and plastic filters.

45. A process according to claim 6 wherein the fumaric acid precipitate is separated by filtration with a sintered metal filter having a pore size of from about 0.02 microns to about 100 microns.

46. A process according to claim 7 wherein the fumaric acid precipitate is separated by filtration with a sintered metal filter having a pore size of from about 0.02 microns to about 100 microns.

47. A process according to claim 6 wherein the fumaric acid precipitate is separated by centrifugation.

48. A process according to claim 7 wherein the fumaric acid precipitate is separated by centrifugation.

49. A process according to claim 1 wherein the fumaric acid precipitate is separated by filtration using at least two filters wherein said filters are alternated to provide continuous operation of the process.

50. A process according to claim 6 wherein the fumaric acid precipitate is separated by filtration using at least two filters wherein said filters are alternated to provide continuous operation of the process.

51. A process according to claim 1 wherein the recovered fumaric acid is further purified by washing with water or another solvent.

52. A process according to claim 6 wherein the recovered fumaric acid is further purified by washing with water or another solvent.

* * * * *

UNITED STATES PATENT AND TRADEMARK OFFICE
CERTIFICATE OF CORRECTION

PATENT NO.: 5,929,255
DATED: July 27, 1999
INVENTOR(S): John M. Forgac

It is certified that error appears in the above-identified patent and that said Letters Patent is hereby corrected as shown below:

Patent reads:

| Col. | Line | |
|------|------|---|
| 2 | 51 | "I. a liquid suspension"<br><br>should read:<br>"i. a liquid suspension" |
| 5 | 1 | "from the from step (c)"<br><br>should read:<br>"from step (c)" |
| 7 | 49 | "rather that incinerated"<br><br>should read:<br>"rather than incinerated" |
| 7 | 54 | "embodiment present invention"<br><br>should read:<br>"embodiment of the present invention" |

UNITED STATES PATENT AND TRADEMARK OFFICE
CERTIFICATE OF CORRECTION

PATENT NO.: 5,929,255
DATED: July 27, 1999
INVENTOR(S): John M. Forgac

It is certified that error appears in the above-identified patent and that said Letters Patent is hereby corrected as shown below:

Patent reads:

| Col. | Line |  |
|------|------|--|
| 8 | 2,3 | "will go the inside" should read: "will go to the inside" |
| 8 | 34 | "31.0 wt % This" should read: "31.0 wt %. This" |
| 8 | 38 | "can however be used" should read: "can, however, be used" |
| 13 | 50 | "In a alternative embodiment" should read: "In an alternative embodiment" |

UNITED STATES PATENT AND TRADEMARK OFFICE
CERTIFICATE OF CORRECTION

PATENT NO.: 5,929,255

DATED: July 27, 1999

INVENTOR(S): John M. Forgac

It is certified that error appears in the above-identified patent and that said Letters Patent is hereby corrected as shown below:

Patent reads:

| Col. | Line | | |
|------|------|---|---|
| 13 | 65 | "the MAN, FA; and o-xylene" should read: "the MAN, FA, and o-xylene" | |
| 16 | 27 | "Alternatively, If the filter" should read: "Alternatively, if the filter" | |
| 16 | 47 | "I.e., it must allow" should read: "i.e., it must allow" | |
| 18 | 19 | "filter as well a the" should read: "filter as well as the" | |

UNITED STATES PATENT AND TRADEMARK OFFICE
CERTIFICATE OF CORRECTION

PATENT NO.: 5,929,255

DATED: July 27, 1999

INVENTOR(S): John M. Forgac

It is certified that error appears in the above-identified patent and that said Letters Patent is hereby corrected as shown below:

Patent reads:

| Col. | Line | | |
|------|------|---|---|
| 19 | 42 | "Aprocess" should read: "A process" | |
| 24 | 8 | "to abut 50 weight" should read: "to about 50 weight" | |
| 24 | 55 | "100 microns." should read: "10 microns." | |

Signed and Sealed this

Fourteenth Day of November, 2000

Attest:

Q. TODD DICKINSON

*Attesting Officer*     *Director of Patents and Trademarks*